United States Patent
Suzuki

(10) Patent No.: US 7,222,963 B2
(45) Date of Patent: May 29, 2007

(54) OPHTHALMIC MEASUREMENT APPARATUS

(75) Inventor: Takayoshi Suzuki, Hamamatsu (JP)

(73) Assignee: Kowa Company Ltd, Aichi (JP)

( * ) Notice: Subject to any disclaimer, the term of this patent is extended or adjusted under 35 U.S.C. 154(b) by 653 days.

(21) Appl. No.: 10/610,620

(22) Filed: Jun. 30, 2003

(65) Prior Publication Data
US 2004/0183997 A1    Sep. 23, 2004

(30) Foreign Application Priority Data
Mar. 17, 2003 (JP) .............................. 2003-071893

(51) Int. Cl.
*A61B 3/14* (2006.01)
(52) U.S. Cl. .................................. 351/209
(58) Field of Classification Search ............... 351/205, 351/209, 210, 221, 246
See application file for complete search history.

(56) References Cited

U.S. PATENT DOCUMENTS

| | | | | |
|---|---|---|---|---|
| 4,900,145 A | * | 2/1990 | Akiyama | ................. 351/221 |
| 5,013,146 A | * | 5/1991 | Akiyama | ................. 351/208 |
| 5,184,157 A | * | 2/1993 | Ichihashi et al. | ......... 351/208 |
| 5,341,180 A | * | 8/1994 | Isogai et al. | ............... 351/206 |
| 5,754,328 A | * | 5/1998 | Cobb et al. | ................. 359/208 |
| 5,757,463 A | * | 5/1998 | Kohayakawa | .............. 351/214 |
| 5,828,481 A | * | 10/1998 | Cobb et al. | ................. 359/208 |
| 5,861,937 A | * | 1/1999 | Fujieda | ..................... 351/204 |
| 6,206,523 B1 | * | 3/2001 | Hino | ......................... 351/212 |
| 6,860,602 B2 | * | 3/2005 | Torii et al. | ................. 351/214 |

FOREIGN PATENT DOCUMENTS

| | | |
|---|---|---|
| JP | 03-264044 | 11/1991 |
| JP | 07-178052 | 7/1995 |
| JP | 09-084763 | 3/1997 |

* cited by examiner

*Primary Examiner*—Timothy Thompson
(74) *Attorney, Agent, or Firm*—Knobbe Martens Olsen & Bear LLP

(57) ABSTRACT

There is provided a technique in which alignment can easily be performed, a period for which the alignment adjustment is completed is shortened, and operability is improved. Alignment is performed using the apex of cornea as a reference by optical structures different from those of the light projection system and the light receiving system. An intersection point of optical axes of the light projection system and the light receiving system in the eye is set to a biological property measurement point in the eye which is shifted by a predetermined distance from the apex of cornea.

11 Claims, 9 Drawing Sheets

FORWARD MOVEMENT

BACKWARD MOVEMENT

OPHTHALMIC MEASUREMENT APPARATUS

BACKGROUND OF THE INVENTION

1. Field of the Invention

The present invention relates to an ophthalmic measurement apparatus for measuring biological properties of an eye to be examined, such as the number of cells floating in an anterior chamber thereof, a protein concentration therein, or the degree of opacity of a crystalline lens by projecting scanning laser light into the eye and by receiving, for example, light scattered from the eye.

2. Description of the Related Art

Up to now, a flare meter and a flare cell meter have been known as ophthalmic measurement apparatuses, in which laser light is irradiated into an anterior chamber of an eye to be examined and scattered light produced by the scattering of the laser light in the anterior chamber of the eye is received, to thereby perform ophthalmic measurement. The flare meter etc can measure the number of floating cells in the anterior chamber of the eye, and the protein concentration (flare concentration) therein by the above-mentioned measurement.

As conventional techniques related to such a flare meter, there are techniques disclosed in JP 03-264044 A, JP 07-178052 A, and JP 09-084763 A.

However, in the conventional ophthalmic measurement apparatus such as the flare meter, a specific optical relationship is constructed, in which laser light is projected to the eye from an oblique direction with respect to the eyeball axis thereof and the reflected light is received. In addition, it is difficult to detect a measurement point in the anterior chamber of the eye. Therefore, in order to perform alignment for positional adjustment between the eye and the measurement apparatus, a skilled technique is required for an examiner, which is very difficult.

According to JP 03-264044 A and JP 07-178052 A, it is considered to determine the state of alignment so as to facilitate the alignment. However, even though the determination of the state of alignment is preferably performed, if the alignment work is not actually facilitated, a long period of time is required to complete the alignment depending on the skill of the examiner.

Thus, if it takes a long period of time for the completion of the alignment, a total time required for the measurement becomes long, with the result that the burden placed on an examinee who must continue to gaze into a point becomes excessively large.

Accordingly, development of such an apparatus with good operability and usability has been desired, in which alignment adjustment can easily be performed in a short period of time without depending on the skill of the examiner.

SUMMARY OF THE INVENTION

The present invention has been made in view of the above-mentioned problems inherent in the conventional art. Therefore, it is an object of the present invention is to provide a technique in which alignment can easily be performed; a time period for the alignment can be shortened; and its operability is improved.

According to the present invention, a structure of alignment control using the apex of cornea as a reference is provided, which is different from a structure of a specific optical relationship in which laser light is obliquely projected to an eye to be examined with respect to the eyeball axis thereof and the reflected light is received by an ophthalmic measurement apparatus such as a flare meter. In addition, the above-mentioned specific optical relationship is adjusted by the alignment using the apex of cornea as the reference.

Here, a factor by which the measurement point in the above-mentioned specific optical relationship can be determined in the alignment using the apex of cornea as the reference resides in that, as data accumulation has progressed in recent years, the measurement point could be found, at which measurement can uniformly be performed with high precision for the eyes of a large number of general examinees.

On the other hand, in the case of the alignment using the apex of cornea as the reference, the virtual image position of a first luminescent spot at the reflection of cornea on the eyeball optical axis of the eye is made to coincide with a predetermined first position determination point in X- and Y-directions vertical to the optical axis, with the result that the alignment adjustments in the X- and Y-directions vertical to the optical axis of the apparatus are enabled. In addition, a position of an obliquely reflected virtual image resulting from a second luminescent spot which entered obliquely into the apex of cornea with respect to the optical axis is captured and the position of the virtual image is made to coincide with a predetermined second position determination point. As a result, the alignment adjustment in the Z-direction parallel to the optical axis of the apparatus is enabled.

In order to achieve the above-mentioned object, according to the present invention, an ophthalmic measurement apparatus for measuring biological properties in an eye to be examined by scanning an inner portion of the eye with light includes:

a light projection system that projects scanning irradiation light, which is irradiated from an oblique direction with respect to an eyeball optical axis of the eye from a light source into the eye;

a light receiving system that receives scattered light produced by scattering of the irradiation light in the eye, which is irradiated from the light projection system;

a unit that performs alignments in X- and Y- directions vertical to the eyeball optical axis of the eye using a virtual image of a first luminescent spot at an reflection of cornea, which is irradiated from the eyeball optical axis of the eye; and a unit that performs alignment in a Z-direction parallel to the eyeball optical axis of the eye by capturing at a predetermined reflection angle a virtual image of a second luminescent spot at the reflection of cornea, which is irradiated at a predetermined incident angle with respect to the eyeball optical axis of the eye, in which alignments are performed using the apex of cornea as a reference by the units that perform the respective alignments to set an intersection point of optical axes of the light projection system and the light receiving system in the eye to a biological property measurement point in the eye which is shifted by a predetermined distance from the apex of cornea.

According to the structure, the units are used, which perform the alignments in the X- and Y-directions and the Z-direction whose optical axes are different from those of the light projection system and the light receiving system for measurement, and which employ the apex of cornea as the reference. Thus, the alignments of the light projection system and the light receiving system for measurement can easily be performed using the apex of cornea as the reference. As a result, a period for the completion of the alignment adjustment can be shortened and the operability can be improved.

In this case, the alignments in the X- and Y-directions are performed with respect to a plane orthogonal to the eyeball optical axis of the eye. For example, the X-direction can be set to the horizontal direction of the apparatus and the Y-direction can be set to the vertical direction of the apparatus.

Also, the alignment in the Z-direction is performed along the eyeball optical axis of the eye and the adjustment is performed in the near-and-far direction with respect to the eye.

The biological property measurement point in the eye, which is set in the present invention is, for example, a point for measuring the number of cells floating in the anterior chamber at an inner position of the anterior chamber of the eye (floating cell measurement), a protein concentration (flare concentration measurement), or the degree of opacity in the anterior chamber, or a point for measuring the degree of opacity of a crystalline lens at a crystalline lens position of the eye.

In the unit that performs the alignment in the Z-direction, a split sensor is used to detect the virtual image. It is desirable that the split sensor has a plurality of output values to detect the completion of the alignment.

According to the structure, a plurality of positions at which the alignment in the Z-direction is completed can be set in accordance with a measurement object. For example, a first position can be set to the inner position of the anterior chamber of the eye and a second position can be set to the crystalline lens position of the eye.

It is desirable that, in the light projection system, a condenser lens is moved in a direction vertical to the optical axis of the light projection system for scanning the irradiation light.

According to the structure, the scanning of the irradiation light is performed by simply moving the condenser lens only. Therefore, the structure may be made simple, thereby achieving a low cost. In addition, even in the case where the irradiation light is scanned in plural directions, a movable condenser lens may only be added. As a result, the modification of the apparatus can readily be realized.

It is desirable that, in the light projection system or the light receiving system, aberration is eliminated using a cylindrical lens or a spherical lens, which is provided with tilting with respect to an optical path.

According to the structure, the aberration can easily be eliminated, thereby being capable of improving its measurement precision. For example, large aberration due to the cornea is caused in the light receiving system. Therefore, when an image of the scattered light is imaged, a large astigmatism is generated. However, the aberration can easily be eliminated by the structure.

Brightness of the surroundings of the apparatus is detected before the start of measurement, and if the brightness of a predetermined value or more is detected, It is desirable that the measurement is not performed.

According to the structure, damage of the light receiving element due to entering of excess light into the light receiving element of the light receiving system used for the measurement can be prevented in advance, which is caused by the rash measurements. In addition, even if the measurement is performed under a circumstance in which the external brightness of the surroundings of the apparatus is too high, the prevention of lowering of the measurement precision for the scattered light being extremely weak light, can be attained. As a result, the measurement precision can be made higher.

It is desirable that the unit that performs the alignments in the X- and Y-directions includes a first image pickup unit for photographing an anterior segment of the eye. Further, the ophthalmic measurement apparatus of the invention preferably includes a display unit that displays the anterior segment of the eye which is photographed by the first image pickup unit upon alignment and displays a measurement result upon measurement.

According to the structure, the examiner may only view the display unit upon alignment and measurement. Therefore, it is unnecessary for the examiner to move the eyepoint to different regions upon alignment and measurement. As a result, the operability for the examiner can be enhanced.

It is desirable that the light receiving system includes a second image pickup unit that photographs an image of a measurement region, and that the image obtained by the second image pickup unit is displayed on the display unit.

According to the structure, the examiner can further view the image of the measurement region in the light receiving system through the display unit. Accordingly, the examiner can perform the confirmation of the measurement region, or the like based on the image without moving the eyepoint. As a result, the operability for the examiner can be enhanced.

It is desirable that the measurement of the biological property in the eye is at least one of measurements of the degree of opacity in the anterior chamber, the number of floating cells in the anterior chamber, or the degree of opacity of the crystalline lens.

DETAILED DESCRIPTION OF THE PREFERRED EMBODIMENT

Hereinafter, an example of a preferred embodiment of the present invention will be described in detail with reference to the drawings.

[Entire Structure]

Figure 1:
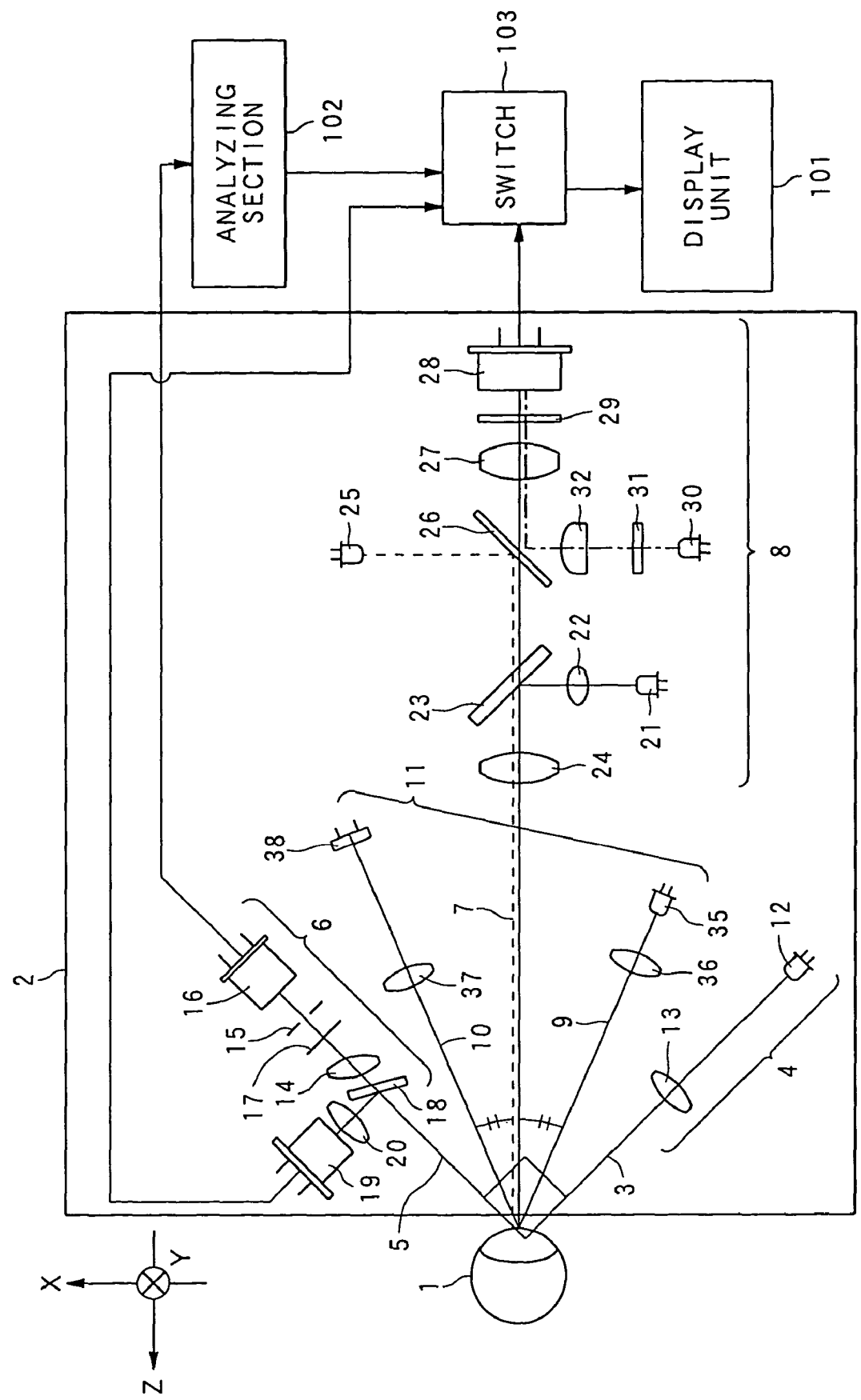
FIG. 1 is a schematic structural diagram showing a laser flare meter (LFM) according to an embodiment.

FIG. 1 is a schematic structural diagram of a laser flare meter (hereinafter referred to as an LFM) according to an embodiment of the present invention. In this embodiment, the LFM will be described as an example of an ophthalmic measurement apparatus. Note that the LFM of this embodiment can measure not only biological properties such as the number of cells floating in the anterior chamber of an eye to be examined (floating cells), a protein concentration (flare concentration) therein, and the level of opacity in the anterior chamber but also a biological property such as the degree of opacity of the crystalline lens of the eye.

In FIG. 1, an eye to be examined 1 as the eyeball of a person to be examined is shown and a measurement section 2 of the LFM is disposed opposite to the eye 1.

The measurement section 2 of the LFM is generally composed of a light projection system 4 disposed along a light projection system optical axis 3, a light receiving system 6 disposed along a light receiving system optical axis 5, an XY-directional alignment adjusting section 8 disposed along a central axis 7 as an eyeball optical axis of the gazing eye to be examined 1, and a Z-directional alignment adjusting section 11 disposed along an incident optical axis 9 and a reflection optical axis 10 for Z-direction.

Also, the LFM includes a main body which is apart from the measurement section 2. The main body is composed of a single display unit 101 for performing various displays on a single screen, an analyzing section 102 for performing various data analyzes and the like, and a switch 103 for changing data displayed on the display unit 101.

Note that, although not described later, the LFM also includes a print output section for printing a measurement result on a sheet such as a paper. Thus, it is needless to say that the measurement result is preserved on the sheet.

Here, with respect to the light projection system optical axis 3 and the light receiving system optical axis 5, an intersection point of both optical axes 3 and 5 is located in a predetermined position in the eyeball of the eye 1, that is, in the anterior chamber of the eye 1. The position of the intersection point indicates a measurement point. An intersection angle at the intersection point of the light projection system optical axis 3 and the light receiving system optical axis 5 is set so as to form a right angle (see FIG. 9A).

On the other hand, the central axis 7 is extended straight from the front of the apex of cornea of the eye 1. The central axis 7 is not overlapped with the light projection system optical axis 3 and the light receiving system optical axis 5 at the intersection point of both optical axes 3 and 5 and shifted therefrom. Note that the central axis 7 generally becomes a single line. However, for description, it is shown for each of optical paths from respective light sources in FIG. 1.

Figure 9A:
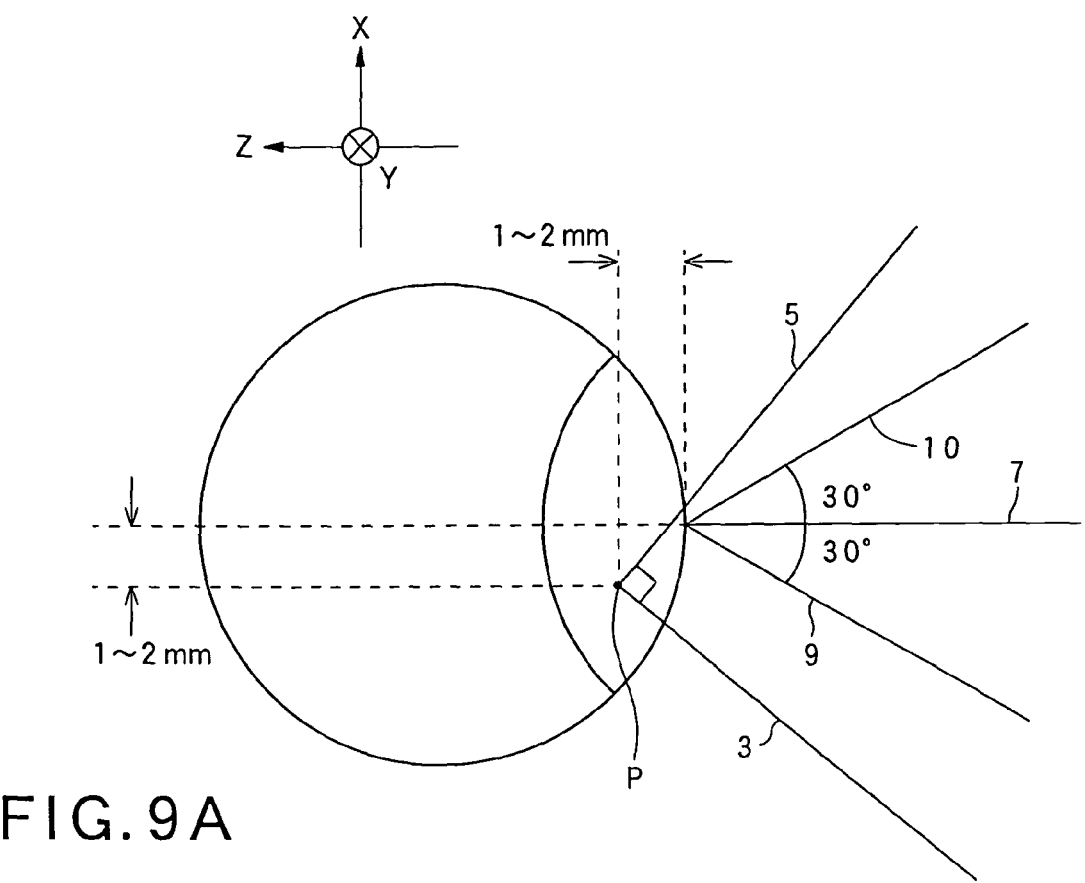
FIGS. 9A and 9B are detail explanatory views of an optical positional relationship between the laser flare meter (LFM) and the eye according to the embodiment.

Also, the incident optical axis 9 and the reflection optical axis 10 for Z-direction intersect with the central axis 7 on the surface of the apex of cornea of the eye 1 and have an incident angle and a reflection angle, respectively, which are substantially symmetric with respect to the central axis 7 (see FIG. 9A).

Note that a relationship between the apex of cornea and the measurement point, which indicates a relationship between the light projection system optical axis 3 and the light receiving system optical axis 5 and the central axis 7 will be described later.

(Light Projection System)

First, the light projection system 4 of the measurement section 2 of the LFM will be described. In the light projection system 4, laser light emitted from a laser light source 12 such as a visible laser diode is projected into the anterior chamber of the eye 1 of a person to be examined through a condenser lens 13 along the light projection system optical axis 3 which is oblique with respect to the central axis 7.

The condenser lens 13 is driven in a direction vertical to the light projection system optical axis 3 (direction vertical to a paper surface in FIG. 1) by a driver unit which is not shown and laser light is finely scanned in one-dimension. Thus, the laser light scanning is performed by only the simple movement of the condenser lens 13. Therefore, the structure of the apparatus is simple, and the number of parts can be reduced, thereby achieving a cost reduction. In addition, even when laser light is scanned in a plurality of directions in order to measure the number of cells floating in the anterior chamber (floating cells) by the laser flare cell meter, only a movable condenser lens is preferably added and the apparatus is readily modified. Further, when compared with the conventional apparatus that uses a galvanomirror the apparatus of this embodiment realizes the following merits: an installation space can be made small because it is unnecessary to refract laser light by a mirror; scanning adjustment is facilitated because it is unnecessary to perform difficult mirror adjustment; and a cost reduction is achieved because it is unnecessary to use an expensive galvanomirror.

Note that, although not provided to the light projection system 4 of this embodiment, in order to eliminate an aberration in the light projection system 4, a cylindrical lens, a spherical lens whose optical axis is tilted with respect to an optical path, or the like can be disposed along the light projection system optical axis 3. When the cylindrical lens, the spherical lens tilted with respect to the optical path, or the like is provided, the aberration can easily be eliminated and measurement precision can be improved.

(Light Receiving System)

Next, the light receiving system 6 will be described. In the light receiving system 6, scattered light in the eye 1 resulting from laser light from the laser light source 12 is detected by a photoelectric detector 16 such as a photomultiplier as a light receiving element through a lens 14 and a light receiving mask 15 which are disposed along the light receiving system optical axis 5 which is oblique with respect to the central axis 7.

An intersection angle formed by the light receiving system optical axis 5 of the light receiving system 6 and the light projection system optical axis 3 is set at a right angle (see FIG. 9A).

The lens 14 is a spherical lens tilted with respect to the optical path. When the light receiving system optical axis 5 for the eye 1 is oblique with respect to the central axis 7, scattered light from a point in the anterior chamber of the eye 1 is refracted in only one direction because a prism effect acts at a time when the light exits the cornea. With respect to the refracted component, because astigmatism which causes such a state that the light cannot be condensed to a point by a normal lens occurs, a specific lens such as the lens 14 is used to eliminate the aberration. Thus, the aberration can easily be eliminated and measurement precision can be improved. Note that a cylindrical lens may be used as the lens 14 to eliminate the aberration.

The light receiving mask 15 is used to limit a field of view in the light receiving system optical axis 5 direction, thereby specifying a measurement range.

The photoelectric detector 16 converts the amount of received light into an electrical signal and outputs it as an output signal.

Note that the scattered light in the eye 1 is, for example, scattered light resulting from proteins present in the anterior chamber of the eye 1, scattered light resulting from cells floating in the anterior chamber (floating cells), or scattered light resulting from the crystalline lens of the eye 1.

Also, in the light receiving system 6, a shutter 17 for blocking the scattered light at the time of non-measurement is disposed between the lens 14 and the light receiving mask 15. The shutter 17 is closed to prevent the scattered light and disturbance light from being received by the photoelectric detector 16.

Then, the output signal from the photoelectric detector 16 which receives the scattered light in the light receiving system 6 is supplied to the analyzing section 102. In the analyzing section 102, a biological property such as a protein concentration is calculated from the output signal related to the scattered light. A measurement result is displayed on the display unit 101 based on the calculation.

The analyzing section 102 analyzes, for example, the output signal digitized using a photon counting method. In the case of the photon counting method, a photo count value is used as an intensity of received light. Each photo count value obtained by scanning laser light is stored in a memory of the analyzing section 102 in time sequence.

In addition, a half mirror 18 for branching an optical path into two, a CCD camera 19 as a second image pickup unit located on an optical path branched by the half mirror 18, and a lens 20 provided in front of the CCD camera 19 are disposed in the light receiving system 6.

The half mirror 18 is disposed on the light receiving system optical axis 5 and tilted at 45° with respect to the light receiving system optical axis 5. Reflected light branched by the half mirror 18 is condensed by the lens 20 and received in the CCD camera 19.

Figure 2:
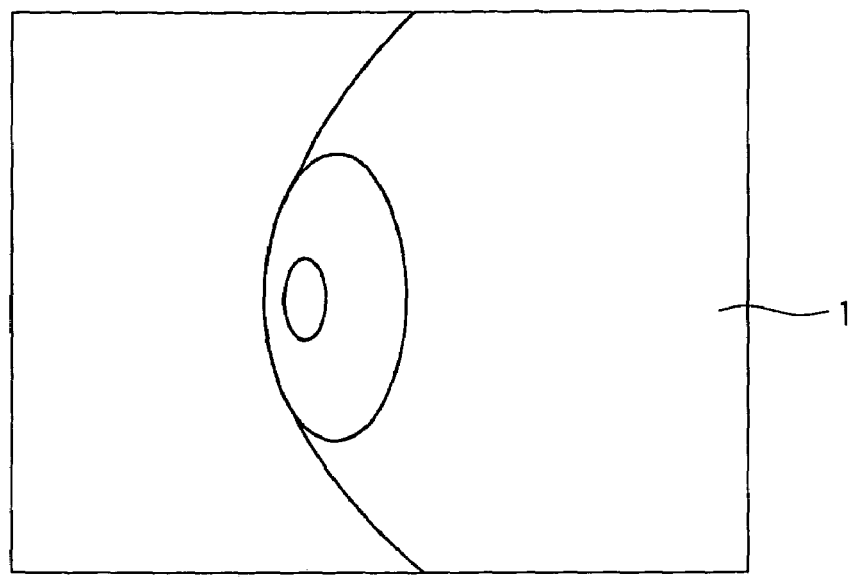
FIG. 2 shows a state in which a measurement region is displayed on a display unit according to the embodiment.

Thus, as shown in FIG. 2, a measurement region of the eye 1 from the light receiving system 6 can be photographed by the CCD camera 19. When the output of the CCD camera 19 is displayed on the display unit 101, a state of the measurement region of the eye 1 can be displayed on the display screen of the display unit 101 and observed.

(XY-Directional Alignment Adjusting Section)

Next, the XY-directional alignment adjusting section 8 will be described. The XY-directional alignment adjusting section 8 has an optical structure in which it is disposed along the central axis 7. In the XY-directional alignment adjusting section 8, illumination light from an illumination light source 21 as an infrared LED is irradiated to the anterior segment of the eye 1, in particular, the apex of cornea through a lens 22, a half mirror 23, and a lens 24 along the central axis 7.

Also, illumination light from an internal fixation lamp 25 as a green LED which is used when a person to be examined gazes into a point is irradiated to the eye 1 through a half mirror 26, the half mirror 23, and the lens 24 along the central axis 7.

Then, the anterior segment image of the eye 1 as reflected light which is obtained by reflecting the illumination light from the illumination light source 21 in the eye 1 along the central axis 7 and which becomes a virtual image of a first luminescent spot at the reflection of cornea travels straight through the lens 24, the half mirror 23, and the half mirror 26 along the central axis 7, and then imaged onto the light receiving surface of a CCD camera 28 as a first image pickup unit composing a light receiving section by a lens 27.

Also, an infrared filter 29 corresponding to the wavelength of the infrared LED of the illumination light source 21 is disposed in front of the light receiving surface of the CCD camera 28 in order to reduce the influence of disturbance light.

Also, illumination light from a light source 30 is received in the CCD camera 28. The light source 30 is an infrared LED for displaying on a screen on which the anterior segment image is displayed a circle which indicates an index for determining a first position determination point at which alignment adjustment by the measurement section 2 of the LFM is possible and which is lighted in a ring-shape.

The illumination light from the light source 30 is received in the CCD camera 28 through a circle display mask 31, a lens 32, the half mirror 26, and the lens 27. Because the light source 30 is also the infrared LED, a circle image from the light source 30 is received in the CCD camera 28 without being removed by the infrared filter 29.

Figure 3:
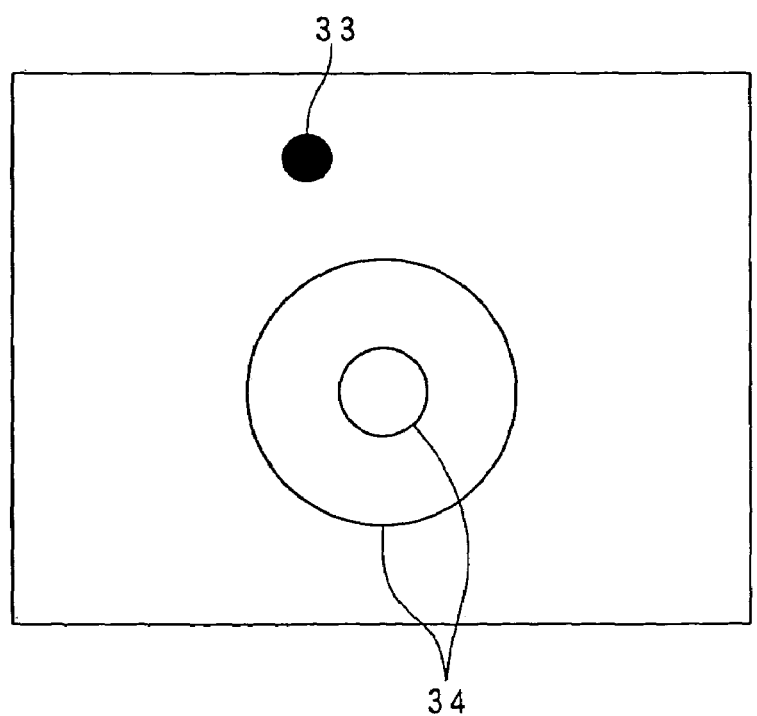
FIG. 3 shows a state in which an anterior segment image of a first luminescent spot of an eye to be examined in alignment adjustment is displayed on the display unit according to the embodiment.

The CCD camera 28 is connected with the display unit 101 through the switcher 103. As shown in FIG. 3, an anterior segment image 33 of a first luminescent spot of the eye 1 and a circle 34 which are received in the CCD camera 28 are displayed on the display screen of the display unit 101.

(Z-Directional Alignment Adjusting Section)

Next, the Z-directional alignment adjusting section 11 will be described. In the Z-directional alignment adjusting section 11, illumination light from a light source 35 as an LED having a wavelength different from that of the illumination light source 21 is irradiated to the cornea of the eye 1 through a lens 36 along an incident optical axis 9.

Then, reflected light which becomes a virtual image of a second luminescent spot on the surface of the cornea is detected through a lens 37 by a two-split sensor 38 such as a two-split type photo diode as a split sensor on the reflection optical axis 10.

The incident optical axis 9 and the reflection optical axis 10 are each set so as to have a substantially symmetric tilt with respect to the central axis 7 using the surface of the apex of cornea as a vertex angle. In this embodiment, the incident optical axis 9 and the reflection optical axis 10 are form an angle of 30° with respect to the central axis 7, respectively (see FIG. 9A).

The two-split sensor 38 determines a distance between the apex of cornea of the eye 1 and the apparatus (in Z-axis direction) from a ratio of the amount of cornea reflection light made incident into a light receiving surface. In the two-split sensor 38, alignment completion points are set to two second position determination points. Note that a plurality of alignment completion points may be further provided.

In this embodiment, the measurement point is set to an inner position of the anterior chamber or a position of the crystalline lens in the eye 1 according to the output of the two-split sensor 38. For example, when an intensity ratio of the two-split sensor 38 is 10:10, the measurement point for protein concentration (flare) is set in the anterior chamber. When the intensity ratio is 5:15, the measurement point for the degree of opacity is set in the crystalline lens. Note that, in this embodiment, the case where adjustment for positioning the measurement point in the inner position of the anterior chamber is performed for measurement is described.

In this embodiment, alignment adjustment with respect to all X-, Y-, and Z-directions is performed according to operation using a joystick 53 by an examiner. However, it may be controlled so as to automatically perform all alignments. In addition, it may be controlled such that rough movement is performed in the X- and Y-directions according to operation using the joystick or the like by the examiner and fine movement is automatically performed.

(Display Unit)

As described above, a measurement result from the analyzing section 102 upon measurement, a state of a measurement region of the eye 1 from the CCD camera 19 upon alignment, or the anterior segment image 33 of the eye 1 and the circle 34 from the CCD camera 28 are displayed on the display unit 101. In other words, switching of three display contents is performed to display any one of the contents. The display switching is performed by the switcher 103 according to the control of the analyzing section 102.

Only one display unit 101 is used. Because switching of the display contents is performed as described above, the examiner only needs to observe the screen of the display unit 101 at all times. Thus, it is unnecessary for the examiner to move the eyepoint to different regions in alignment and measurement, so that the operability for the examiner can be improved.

(Analyzing Section)

The analyzing section 102 is a so-called computer-control section. In other words, the analyzing section 102 includes a CPU for executing processing such as analyzing operation based on a program stored in advance, a memory for temporarily storing output signal data, a processing result, and the like and temporarily storing a computation result for processing and the like, and a storage device such as an EPROM or a HDD for storing the output signal data, the processing result, and the like.

The analyzing section 102 performs not only analyzing of the output signal but also switching of display objects to be displayed on the display unit 101 by controlling the switcher 103 in accordance with input from the examiner particularly upon alignment adjustment as well as control for driving a drive motor according to input operation using the joystick or the like by the examiner.

[Overview of Apparatus]

Figure 4:
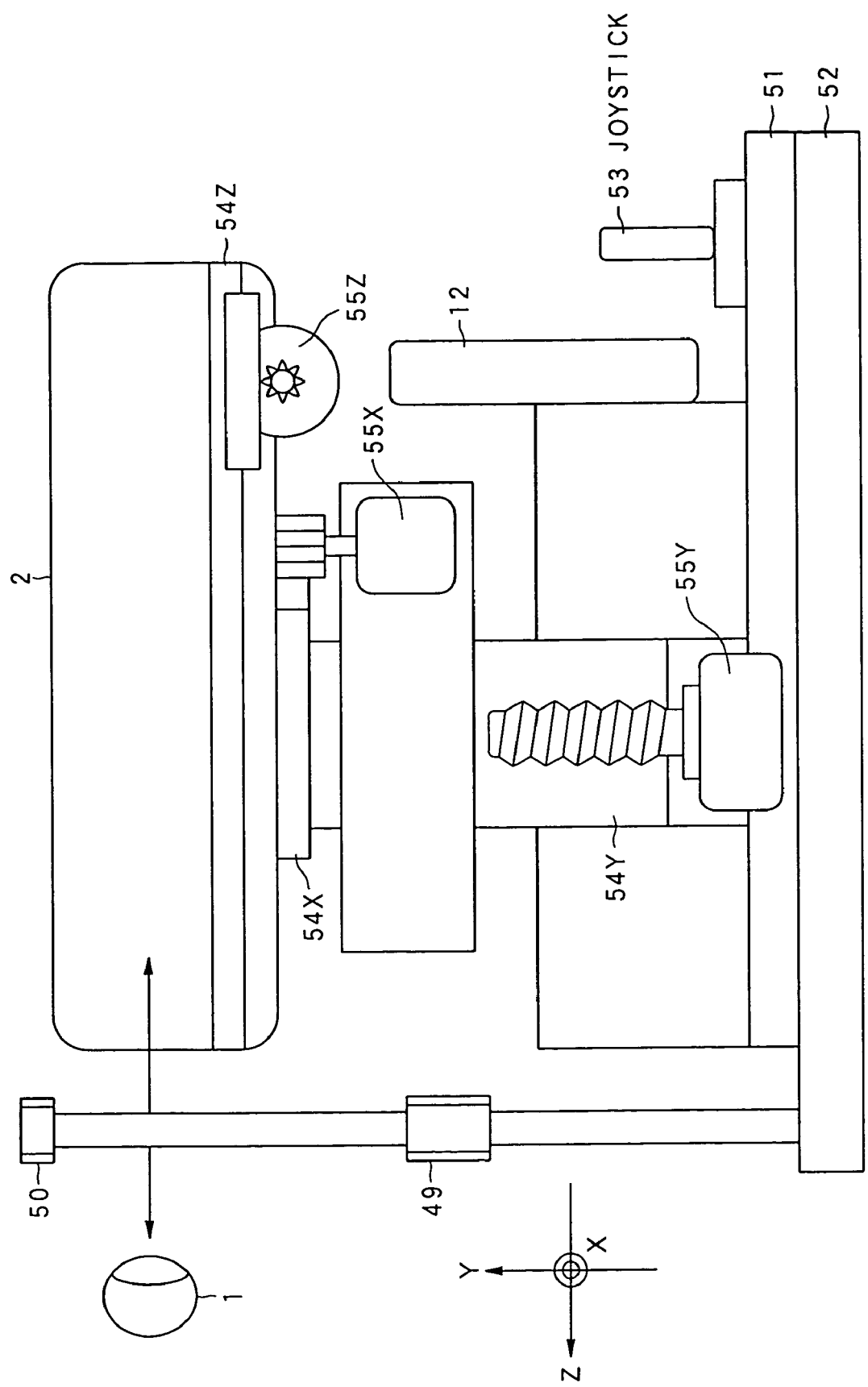
FIG. 4 is an outline view of the laser flare meter (LFM) according to the embodiment.

FIG. 4 is an outline view showing a summary of apparatus of the LFM according to this embodiment.

The LFM includes a chin stand 49 and a forehead holder 50 for supporting the head of a person to be examined and opposing the eye 1 to the measurement section 2 of the LFM.

A movable base 51 of the LFM is provided on a pedestal portion 52 and includes a joystick 53 capable of moving the measurement section 2 of the LFM which is located over the movable base 51.

Further, only one display unit 101 is located to the movable base 51. The examiner mainly views the display screen of the display unit 101 to perform the operation of the apparatus. In addition, although not shown, the movable base 51 includes various operating buttons such as a measurement start button and a power source switch in addition to the joystick 53.

Figure 5:
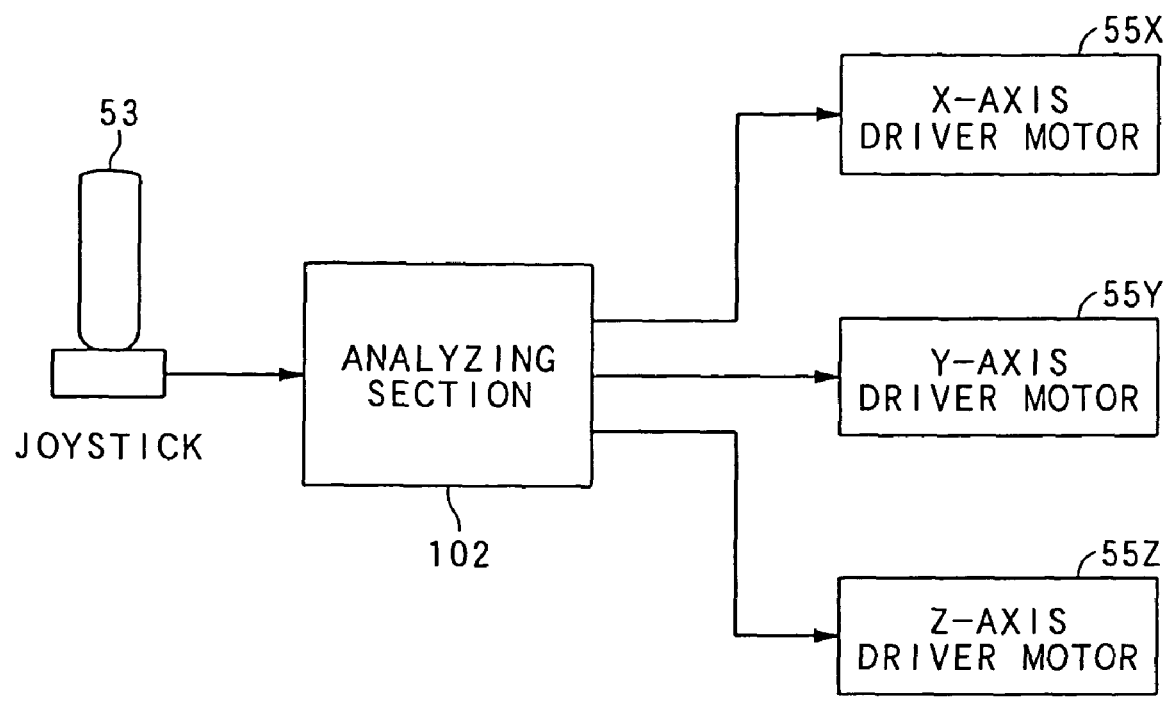
FIG. 5 is a block diagram showing drive control with respect to X-, Y-, and Z-axes according to the embodiment.

Positioning of the measurement section 2 of the LFM with respect to the eye 1 is performed by converting the operation using the joystick 53 into an action of gears connected with the respective drive motors 55X, 55Y, and 55Z through the analyzing section 102 to actuate the measurement section 2 in three-dimensional direction of X-, Y-, and Z-axes along rails 54X, 54Y, and 54Z as shown in FIG. 5.

[Measurement]

Next, measurement using the LFM will be described. The measurement is generally performed according to a flow chart shown in FIG. 6. The measurement is generally divided into the alignment adjustment before the start of the measurement and the execution of the measurement.

[Alignment Adjustment]

First, the case where the alignment adjustment is performed for the eye 1 will be described.

With respect to the alignment adjustment, the XY-directional alignment adjustment and the Z-directional alignment adjustment are performed by the XY-directional alignment adjusting section 8 and the Z-directional alignment adjusting section 11.

(XY-Directional Alignment Adjustment)

Here, first, the XY-directional alignment adjustment which is performed earlier will be described. The XY-directional alignment adjustment is performed using the XY-directional alignment adjusting section 8.

When the XY-directional alignment adjustment is performed, the anterior segment image 33 of the eye 1 and the circle 34 which are received in the CCD camera 28 and displayed on the display unit 101 are used, and the anterior segment image 33 is moved in the X- and Y-directions vertical to the central axis 7 such that it is aligned within the circle 34.

First, in step S101 (see FIG. 6), the illumination light source 21 is turned on, reflection light reflected at the apex of cornea of the eye 1, which is resulted from light from the illumination light source 21, is received in the CCD camera 28, and the anterior segment image 33 of the eye 1 is displayed on the display screen of the display unit 101. In addition, similarly, the circle 34 indicating the position of the measurement section 2 of the LFM is also received and displayed on the display screen of the display unit 101 (see FIG. 3).

Then, in step S102 (see FIG. 6), while viewing the anterior segment image 33 of the eye 1 and the circle 34 displayed on the display unit 101, an examiner makes the anterior segment image 33 fall within the circle 34 using the joystick 53.

Figure 7:
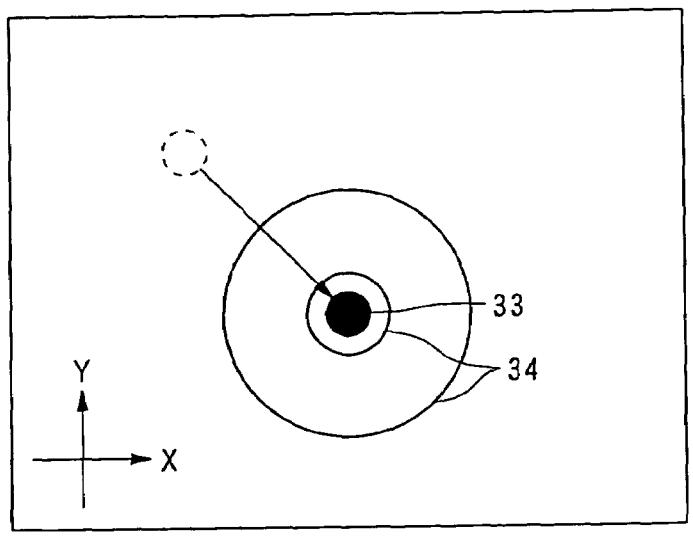
FIG. 7 shows a state of the display unit in XY-directional alignment adjustment according to the embodiment.

In other word, as shown in FIG. 7, an input operating signal from the joystick 53 is inputted to the analyzing section 102, and two drive motors, the X-axis drive motor 55X and the Y-axis drive motor 55Y, which are provided for movement in the X- and Y-directions are driven by the analyzing section 102. Thus, the measurement section 2 of the LFM is moved in the vertical and horizontal directions to make the anterior segment image 33 fall within the circle 34 (first position determination point) as indicated by an arrow in the drawing.

Note that, in this embodiment, the X-direction is set to the horizontal (right-and-left) direction of the LFM and the Y-direction is set to the vertical (up-and-down) direction of the LFM.

With respect to specific movement of the measurement section 2 of the LFM from right to left and up and down, the movement in the right-to-left direction is performed by an operation in which the joystick 53 is tilted from right to left. In addition, the movement in the up-and-down direction is performed by an operation in which a control knob as the grip portion of the joystick 53 is rotated.

(Z-Directional Alignment Adjustment)

After the XY-directional alignment adjustment is completed, the Z-directional alignment adjustment is next performed.

The Z-directional alignment adjustment is performed using the Z-directional alignment adjusting section 11.

In the Z-directional alignment adjustment, the output value of the two-split sensor 38 in which adjustment is completed is set in advance. Thus, the measurement section 2 of the LFM is moved back and forth in the Z-direction with respect to a measurement object of the eye 1, that is, in the near-and-far direction with respect to the eye 1.

In step S103 (see FIG. 6), while viewing the display unit 101, an examiner performs an operation according to a forward movement instruction 39 or a backward movement instruction 40 which are displayed on the display unit 101 using the joystick 53.

Figure 8A:
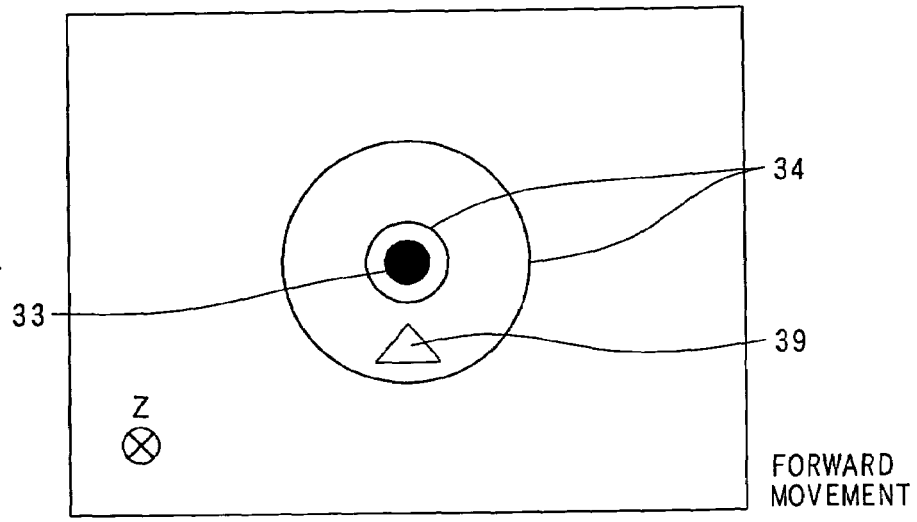
FIGS. 8A and 8B show states of the display unit in a Z-directional alignment adjustment according to the embodiment.
Figure 8B:
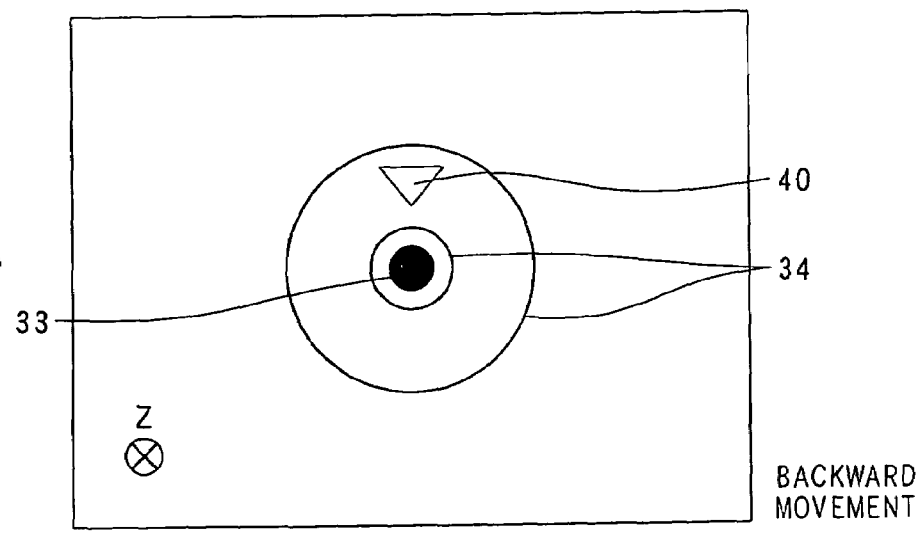

With respect to a state of the display screen of the display unit 101, FIG. 8A shows a state in which the forward movement instruction 39 is displayed and FIG. 8B shows a state in which the backward movement instruction 40 is displayed.

According to the forward movement instruction 39 is displayed or the backward movement instruction 40 displayed on the display screen, an input operating signal from the joystick 53 is inputted to the analyzing section 102, and only the Z-axis drive motor 55Z provided for movement in the Z-direction is driven by the analyzing section 102. Thus, the measurement section 2 of the LFM is moved back and forth with respect to the eye 1 to be positioned in predetermined back-and-forth second position determination points. When it is located in the back-and-forth second position determination points, for example, a buzzer is sounded or a message indicating the determination completion is displayed so as to inform the examiner of the completion of the adjustment.

The specific back-and-forth movement of the measurement section 2 of the LFM is performed by an operation in which the joystick 53 is tilted back and forth.

Note that the forward movement instruction 39 or the backward movement instruction 40 displayed on the display unit 101 is displayed according to determination of the analyzing section 102 based on the output value of the two-split sensor 38. In addition, when the measurement section 2 of the LFM excessively approaches the eye 1, the analyzing section 102 performs control to issue an alarm sound for notice.

[Relationship between Alignment using Apex of Cornea as Reference and Measurement Point]

Now, for the measurement using the LFM, it is required that laser light from the laser light source 12 is always irradiated to a predetermined searching region of the eye 1. If a displacement between the eye 1 and the light projection system 4 or the light receiving system 6 is caused, unnecessary stray light component resulting from cornea reflection, iris reflection or the like is mixed into a detection signal to cause a measurement error.

Thus, it is required that alignments of the light projection system 4 and the light receiving system 6 in the measurement section 2 of the LFM with the measurement points are accurately set by the alignment adjustment. The systems are constructed according to the specific optical relationship.

Therefore, in this embodiment, when the above-mentioned alignment of the measurement section 2 of the LFM using the apex of the cornea as the reference is completed, setting is performed such that an intersection point of the light projection system optical axis 3 and the light receiving system optical axis 5 in the measurement section 2 of the LFM is located at a predetermined measurement point in the eye 1.

Figure 9B:
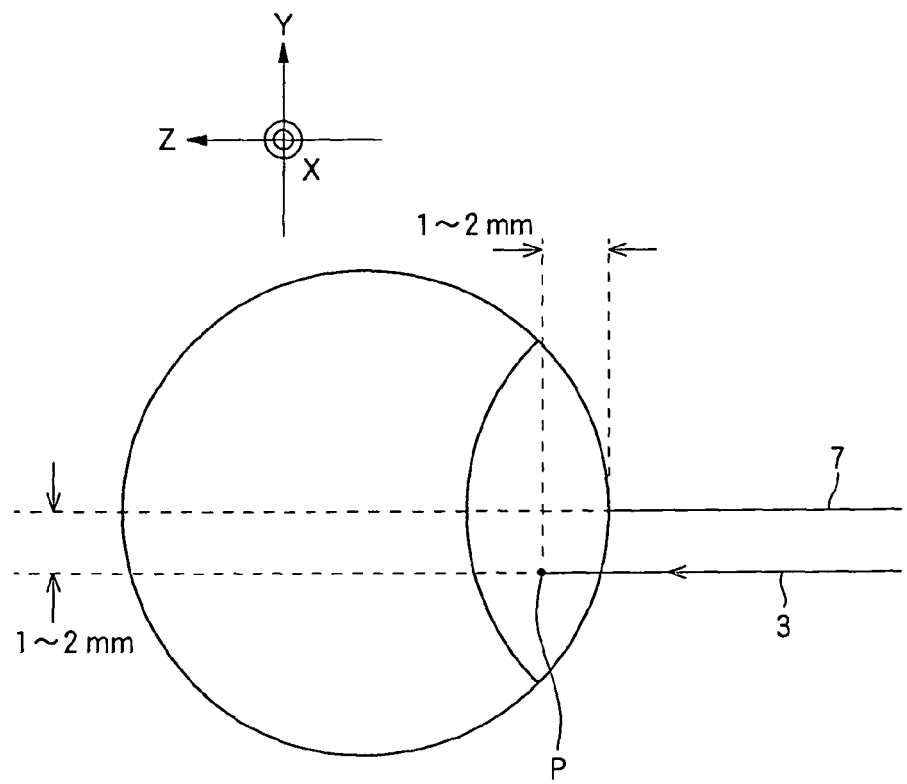

As shown in FIGS. 9A and 9B, as a specific example, when the alignment using the apex of the cornea as the reference is completed, the intersection point is located at a measurement point P in the anterior chamber of the eye 1. The measurement point P in the anterior chamber is located on the light projection system optical axis 3 side at a distance of 1 mm to 2 mm from the central axis 7 of the apex of the cornea with respect to the X-direction (see FIG. 9A), located on underside of the central axis 7 of the apex of the cornea at a distance of 1 mm to 2 mm therefrom with respect to the Y-direction (see FIG. 9B), and located in the eye fundus side at a distance of 1 mm to 2 mm from the apex of the cornea with respect to the Z-direction (see FIGS. 9A and 9B).

Such a measurement point of the eye 1 is determined because it is now apparent that high precision measurement is possible while uniformly preventing harmful light from entering the eyes to be examined 1 of a large number of persons based on data accumulated up to now.

In other words, the intersection angle at the intersection point of the light projection system optical axis 3 and the light receiving system optical axis 5 forms a right angle in order to prevent "crystalline lens scattered light" from existing in entering the background of the measurement region and to make a light flux size of laser light within the measurement region uniform. The reason why the measurement point P with respect to the X-direction is located on the light projection system optical axis 3 side at a distance of 1 mm to 2 mm from the central axis 7 of the apex of the cornea is to cause a displacement in laser light made incident from an oblique direction with respect to the central axis 7 without making the light pass through the apex of cornea when the laser light exists at a farthest distance from the iris of the eye 1 in order to prevent "iris scattered light". The measurement point P with respect to the Y-direction is located on underside of the central axis 7 of the apex of the cornea at a distance of 1 mm to 2 mm therefrom in order to prevent "light reflected on the surface of cornea which is resulted from scattered light in the exit of the light projection system". The measurement point P with respect to the Z-direction is located on the eye fundus side at a distance of 1 mm to 2 mm from the apex of the cornea in order to locate the point in an intermediate position of positions at which each of the "cornea scattered light" and "crystalline lens scattered light" is fully prevented. Thus, conventional operation in which the examiner determines a measurement point according to each person to be examined becomes unnecessary. Therefore, harmful light such as "crystalline lens scattered light", "iris scattered light", "light reflected on the surface of cornea which is resulted from scattered light in the exit of the light projection system", and "cornea scattered light" can be uniformly prevented from entering the eye 1 of a large number of persons, so that high precision measurement becomes possible.

[Execution of Measurement]

Next, after the completion of the alignment, measurement is actually started. The measurement is started when the examiner pushes the measurement start bottom. Alternatively, it is possible to provide a program that forcedly starts the measurement after the completion of the alignment.

(Check of Disturbance)

First, in step S104 (see FIG. 6), the brightness of the surroundings of the apparatus is checked in consideration of an influence of disturbance before the start of the measurement.

The brightness of the surroundings of the apparatus is determined based on whether or not the amount of disturbance light received by the photoelectric detector 16 exceeds the predetermined measurable amount of light when the shutter 17 of the light receiving system 6 is opened without irradiating laser light.

Figure 6:
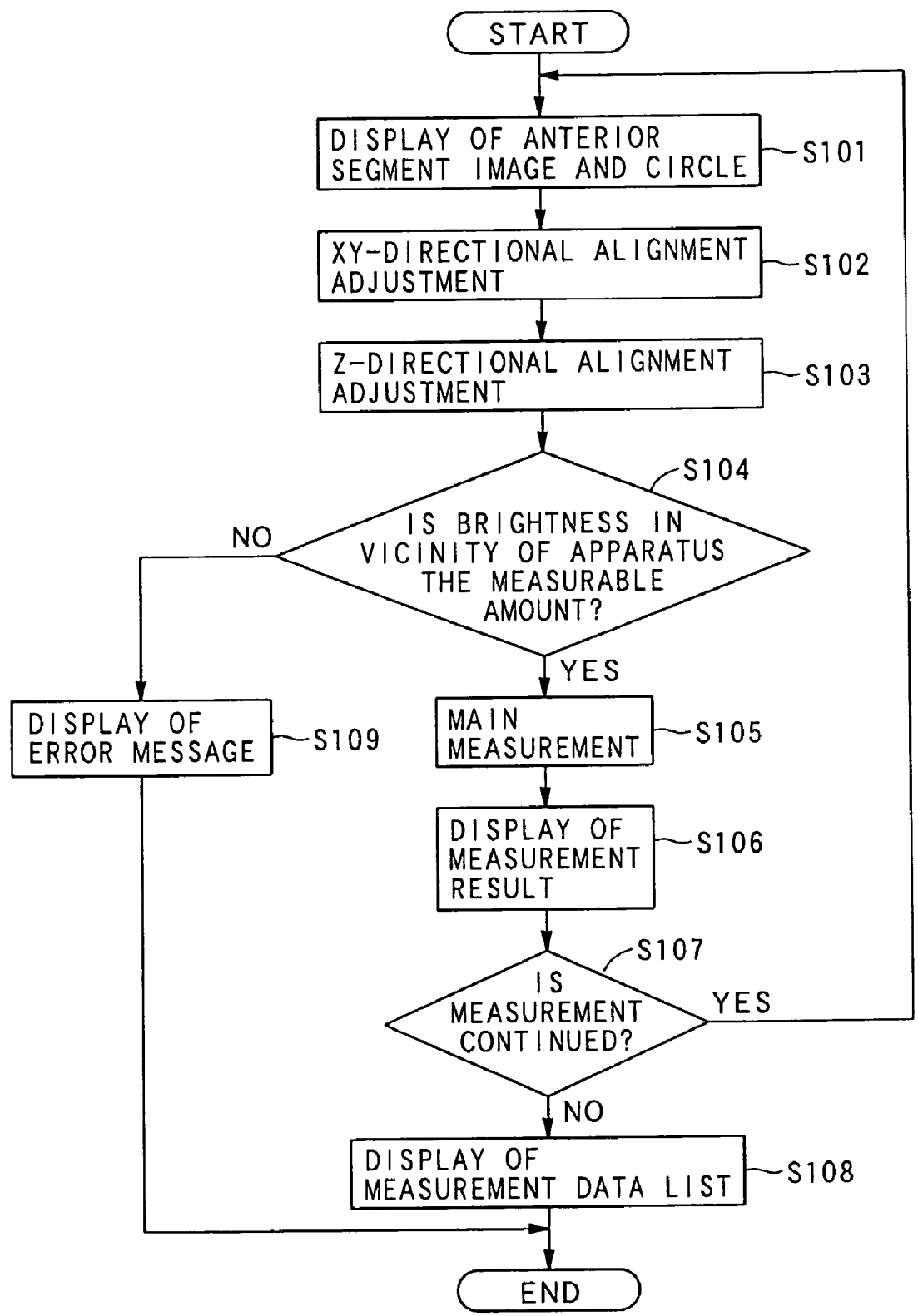
FIG. 6 is a flow chart showing a flow of measurement according to the embodiment.

When the measurement is impossible, the shutter 17 is closed and processing advances to step S109 (see FIG. 6). In step S109 (see FIG. 6), an error message indicating that the measurement is impossible is displayed on the display unit 101. Then, the measurement is terminated after the display of the error message.

As described above, when the brightness of the surroundings of the apparatus exceeds the predetermined amount, the measurement is not performed. Thus, it can be prevented in advance that the measurement is unnecessarily performed to damage the photoelectric detector 16 due to entering of excess light into the photoelectric detector 16 of the light receiving system 6 which is used for the measurement. In addition, it is prevented that the measurement is performed with a state in which the external brightness of the surroundings of the apparatus is too high to reduce measurement precision of scattered light as extremely weak light. Accordingly, the measurement precision can be improved.

(Main Measurement)

On the other hand, when the measurement is possible in step S104 (see FIG. 6), processing advances to step S105 (see FIG. 6). In step S105 (see FIG. 6), the irradiation of laser light from the laser light source 12 of the light projection system 4 is started to start the main measurement.

An irradiation start point of the laser light is set to a position outside the measurement region by scanning the condenser lens 13. The irradiation of laser light to the eye 1 which crosses the measurement region is performed by one-dimensional fine scanning of the condenser lens 13.

Thus, in the light receiving system 6, scattered light in the eye 1 which resulted from the irradiated laser light is detected within a region which crosses the measurement region by the photoelectric detector 16.

(Intensity of Scattered Light)

Figure 10:
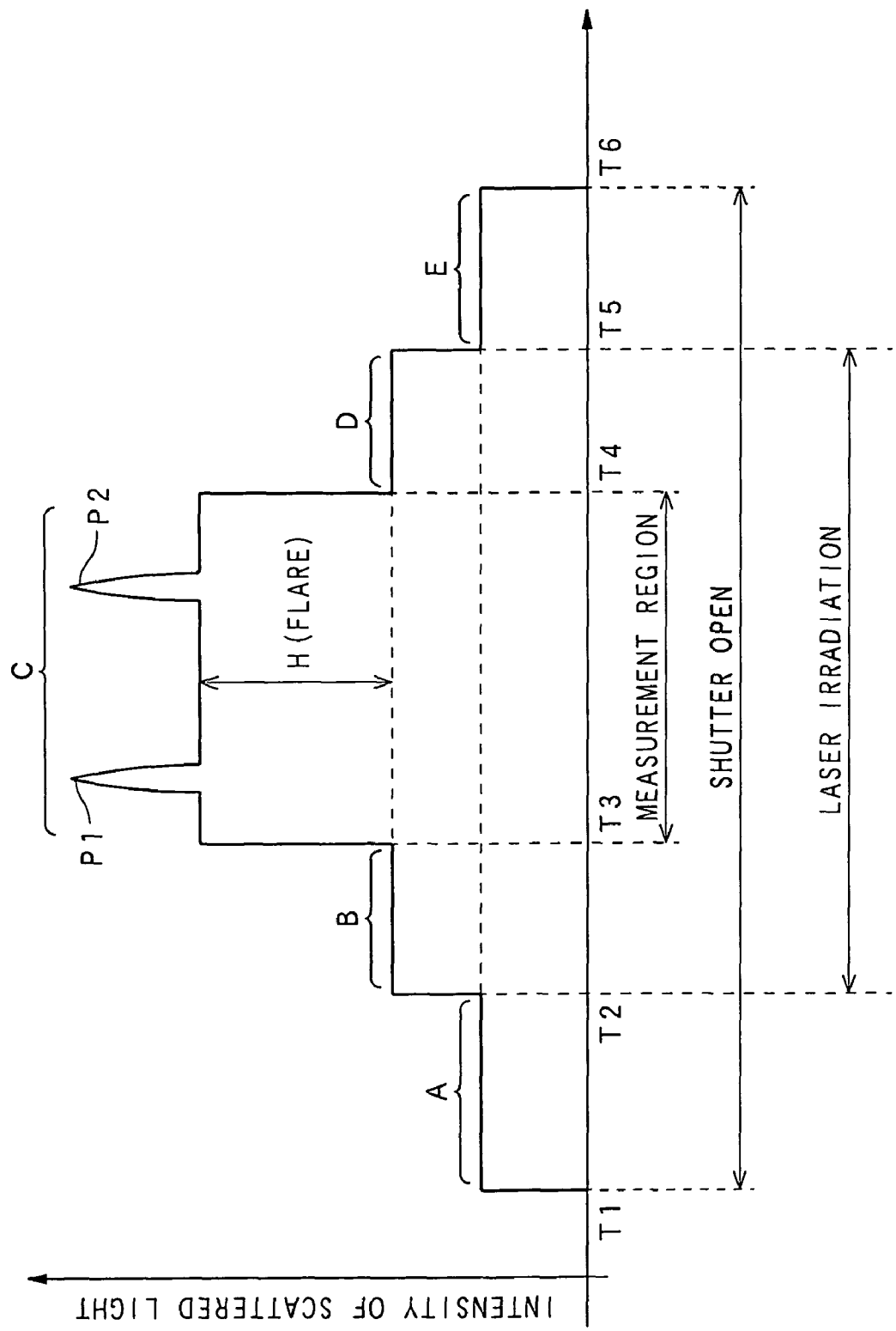
FIG. 10 is a graph showing a time change in intensity of scattered light detected by a photoelectric detector according to the embodiment.

The intensities of scattered light detected by the photoelectric detector 16 are indicated by a graph shown in FIG. 10. Here, the graph shown in FIG. 10 indicates the intensities after a time T1 when the shutter 17 is first opened. The intensities of the scattered light at a time T2 when the irradiation of laser light is started, a time T3 when the irradiation to the measurement region is started, a time T4 when the irradiation to the measurement region is completed, a time T5 when the irradiation of the laser light is completed, and a time T6 when the shutter 17 is closed are indicated in time series in the graph.

In FIG. 10, areas A and E indicate the intensities of the laser light resulting from disturbance which are detected by the photoelectric detector 16. Areas B and D indicate the intensities of the laser light resulting from disturbance which are not scanned in the measurement region yet (background value), although the laser light is irradiated. An area C indicates the intensity of the laser light during measurement in which the laser light is actually scanned in the measurement region.

In the area C, a height H indicates a flare value which is a protein concentration in the anterior chamber of the eye 1. In addition, partial protrusions P1 and P2 indicate cells floating in the anterior chamber of the eye 1 (floating cells).

(Display of Measurement Result)

Figures 11, 12:
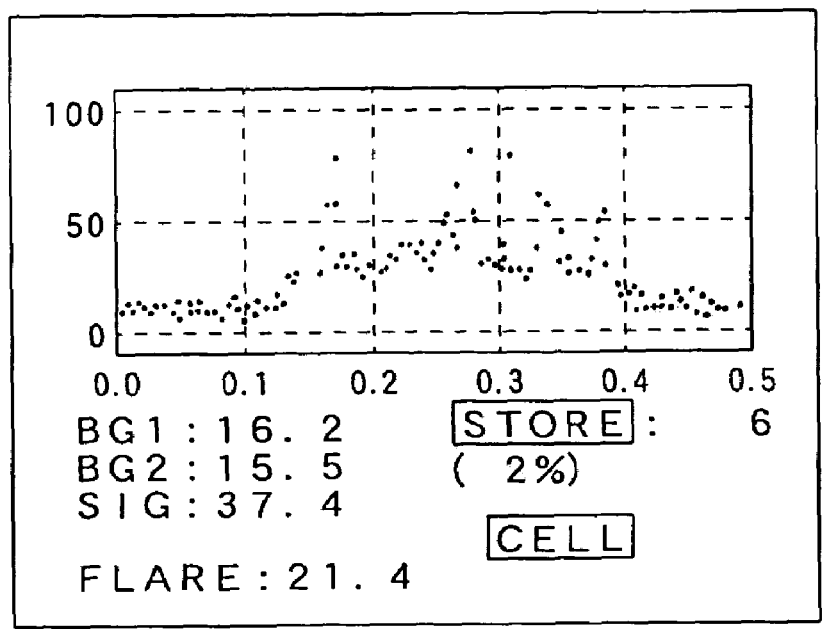
FIG. 11 shows a state in which a measurement result is displayed on the display unit according to the embodiment.
FIG. 12 shows a state in which a measurement data list is displayed on the display unit according to the embodiment.

When the measurement in step S105 (see FIG. 6) is completed, processing advances to step S106 (see FIG. 6). The output signal of the photoelectric detector 16 is analyzed by the analyzing section 102 and a measurement result as shown in FIG. 11 is displayed as a display content on the display unit 101. The display of the display unit 101 is changed from the display of image taken by the CCD camera 28 to the display of data stored in the analyzing section 102 by controlling the switcher 103 by the analyzing section 102.

(Determination of Whether or not Measurement is Continued)

Then, after the measurement result is displayed on the display unit 101 in step S106 (see FIG. 6), it is determined whether or not the measurement is continued in step S107 (see FIG. 6).

When the measurement is continued, processing returns to step S101 (see FIG. 6) and processing from alignment adjustment is performed again.

(Display of Measurement Data List)

On the other hand, when the measurement is completed in step S107 (see FIG. 6), processing advances to step S108 (see FIG. 6) and a list of measurement data stored in the memory of the analyzing section 102 as shown in FIG. 12 is displayed as a display content on the display unit 101. Data displayed on the display unit 101 is internally changed from the display of the measurement result shown in FIG. 11 by the analyzing section 102.

Note that, in this case or immediately after the measurement, the measurement result and the measurement data list may be printed.

Thus, the measurement according to the flow chart shown in FIG. 6 is completed.

[Effect]

As described above, according to this embodiment, the XY-directional and Z-directional alignment adjusting sections 8 and 11 whose optical axes are different from those of the light projection system 4 and the light receiving system 6 for measurement and which employ the apex of cornea as the reference are used. Thus, the alignments of the light projection system 4 and the light receiving system 6 for measurement can easily be performed using the apex of cornea as the reference, so that a period for which the alignment adjustment is completed can be shortened and the operability can be improved.

Also, because the alignment adjustment is performed with high precision, the measurement precision can be improved.

What is claimed is:

1. An ophthalmic measurement apparatus for measuring biological properties in an eye to be examined by scanning an inner portion of the eye with light, comprising:

a light projection system that projects scanning irradiation light, which is irradiated from an oblique direction with respect to an eyeball optical axis of the eye from a light source into the eye;

a light receiving system that receives scattered light produced by scattering of the irradiation light in the eye, which is irradiated from the light projection system;

a unit that performs alignments in X- and Y-directions vertical to the eyeball optical axis of the eye using a virtual image of a first luminescent spot at an apex of cornea, which is irradiated from the eyeball optical axis of the eye; and a unit that performs alignment in a Z-direction parallel to the eyeball optical axis of the eye by capturing at a predetermined reflection angle a virtual image of a second luminescent spot at the apex of cornea, which is irradiated at a predetermined incident angle with respect to the eyeball optical axis of the eye, wherein alignments are performed using the apex of cornea as a reference by the units that perform the respective alignments to set an intersection point of optical axes of the light projection system and the light receiving system in the eye to a biological property measurement point in the eye which is shifted by a predetermined distance from the apex of cornea.

2. An ophthalmic measurement apparatus according to claim 1, wherein the unit that performs the alignment in the Z-direction comprises a split sensor configured to detect the virtual image, and wherein the split sensor has a plurality of output values to detect the completion of the alignment.

3. An ophthalmic measurement apparatus according to claim 1, wherein the light projection system comprises a condenser lens configured to move in a direction vertical to the optical axis of the light projection system for scanning the irradiation light.

4. An ophthalmic measurement apparatus according to claim 1, wherein in one of the light projection system and the light receiving system, aberration is eliminated using one of a cylindrical lens and a spherical lens provided with tilting with respect to an optical path.

5. An ophthalmic measurement apparatus according to claim 1, wherein brightness of the surroundings of the apparatus is detected before the start of measurement, and the measurement is not performed when the brightness of a predetermined value or more is detected.

6. An ophthalmic measurement apparatus according to claim 1,
wherein the unit that performs the alignments in the X- and Y-directions comprises a first image pickup unit for photographing an anterior segment of the eye,
the apparatus further comprising a display unit that displays the anterior segment of the eye which is photographed by the first image pickup unit upon alignment and displays a measurement result upon measurement.

7. An ophthalmic measurement apparatus according to claim 6,
wherein the light receiving system comprises a second image pickup unit that photographs an image of a measurement region of the eye, and
wherein the image obtained by the second image pickup unit is displayed on the display unit.

8. An ophthalmic measurement apparatus according to claim 1, wherein the measurement of the biological property in the eye is at least one of measurements of a degree of opacity in the anterior chamber, number of floating cells in the anterior chamber, or a degree of opacity of the crystalline lens.

9. An ophthalmic measurement method of measuring biological properties in an eye to be examined by scanning an inner portion of the eye with light, the method comprising:
projecting scanning irradiation light, which is irradiated from an oblique direction with respect to an eyeball optical axis of the eye from a light source into the eye;
receiving scattered light produced by scattering of the irradiation light in the eye, which is irradiated from the light source;
performing alignments in X- and Y-directions vertical to the eyeball optical axis of the eye with a virtual image of a first luminescent spot at an apex of cornea, which is irradiated from the eyeball optical axis of the eye; and
performing alignment in a Z-direction parallel to the eyeball optical axis of the eye by capturing at a predetermined reflection angle a virtual image of a second luminescent spot at the apex of cornea, which is irradiated at a predetermined incident angle with respect to the eyeball optical axis of the eye,
wherein alignments are performed using the apex of the cornea as a reference so as to set an intersection point of optical axes of the scanning irradiation light and the scattered light in the eye to a biological property measurement point in the eye which is shifted by a predetermined distance from the apex of the cornea.

10. The method of claim 9, further comprising eliminating aberration with one of a cylindrical lens and a spherical lens provided with tilting with respect to an optical path.

11. The method of claim 9, further comprising detecting brightness of the surroundings before the start of measurement, and wherein the measurement is not performed when the brightness of a predetermined value or more is detected.

* * * * *